United States Patent [19]

Foxwell et al.

[11] Patent Number: 5,583,212
[45] Date of Patent: Dec. 10, 1996

[54] (GAMMA)-[$^{32}$P](GAMMA)-THIORIBONUCLEOSIDE-5'-TRIPHOSPHATES

[75] Inventors: Brian M. J. Foxwell, Hounslow; Peter Parker, Ashstead; Andrew M. Creighton, London, all of United Kingdom

[73] Assignee: British Technology Group Limited, London, England

[21] Appl. No.: 308,451

[22] Filed: Sep. 19, 1994

Related U.S. Application Data

[63] Continuation of Ser. No. 77,962, Jun. 18, 1993, abandoned, which is a continuation of Ser. No. 768,572, Sep. 23, 1991, abandoned.

[30] Foreign Application Priority Data

Mar. 23, 1989 [GB] United Kingdom .................. 8906708

[51] Int. Cl.$^6$ .................................................. C07H 19/20
[52] U.S. Cl. .......................................................... 536/26.26
[58] Field of Search ........................... 536/26.26; 435/89; 424/9; 514/47

[56] References Cited

U.S. PATENT DOCUMENTS 4,728,730  3/1988  Frey et al. ........................... 536/26.12

FOREIGN PATENT DOCUMENTS

| 0214014 | 3/1987 | European Pat. Off. . |
| 2585724 | 2/1987 | France . |
| 2161484 | of 1986 | United Kingdom . |
| 2186579 | of 1987 | United Kingdom . |
| 9011289 | 10/1990 | WIPO . |

OTHER PUBLICATIONS

Cassidy et al. "Enzymatic preparation . . . " Biochimica et Biophysica Acta, 565 (1979), pp. 209–213.
Eckstein "Phosphorothioate Analogues . . . " Accounts of Chem: research vol. 12, No. 6 (1979 Jun.).
Cassel et al. 1982. PNAS, 79:2231, Resistance . . . membranes.
Harris et al. 1993 Tibtech, 11:42, Therapeutic . . . Age.
Osband et al, 1990 Immunology Today, 11:193, Problems . . . Immunotherapy.
Hird et al, Immunotherapy . . . Antibodies, pp. 183–189, 1990.
Walseth et al., "The Enzymatic Preparation of [α-$^{32}$p] Nucleoside Triphosphates, Cyclic [$^{32}$p]AMP, and Cyclic [32p]GMP," Biochem. Biophys. Acta, 526, 11–31 (1979).
Hanker, "The Enzymatic Synthesis of [γ-32p] ATP and [U–14C] ATPγS," Radioisotopy, 31(5–6), 213–220 (1990).
Weber et al., "A Radiometric Method for the Determination of NADH in Subpicomole Amounts," J. Biochemical and Biophysical Methods, 15, 295–306 (1988).

Asante et al., "Polyacrylamide Gel Electrophoresis and Subsection of Total Cell Proteins for Multi–Antibiotic–Resistant Skin Diphtheroids Labelled with [$^{35}$S] Thio ATP and of Coagulase Negative Staphlocci Labeled with [$^{35}$S] Methionine," J. Microbiol. Meth., 7(4/5). 157–167 (1987).
Iyengar et al., "mevalonate–5–diphosphate Decarboxylase: Stereochemical Course of ATP–Dependent Phosphorylation of Mevalonate 5–Diphosphate," Biochemistry, 25(16), 4693–4698 (1986).
Bethell et al., "A New Synthesis of Adenosine 5'–([γ(R)–$^{17}$O, $^{18}$O]–γ–Thiotriphosphate) and Its Use To Determine theStereochemical Course of the Activation of Glutamate by Glutamine Synthetase," Biochemistry, 27(4), 1125–1131 (1988).
Abril et al., "Practical Enzymatic Synthesis of Adenosine 5'–O–(3–Thiotriphosphate (ATP–γ–S)," J. Org. Chem., 49(8), 1360–1364 (1984).
Creighton et al., "The Development of $^{32}$p Technology for Radioimmunotherapy," Ch. 11 in Monoclonal Antibodies 2, A. A. Epenetos (ed.), Chapman & Hall Medical, London, UK, 1993, pp. 103–109.
H. Band et al., "Radioimmunotargeting: Thiophosphorylation for Enhancing the Metabolic Stability of 32P–Labelled Conjugates,"Abstract from 7th Ann. Intl. Hannesmith Conference on Advances in the Application of Monocolonal Antibodies in Clinical Oncology, London, UK, 1990, pp. 183–189.
(Sigma (I)), Biochemicals, Organic Compounds for Research and Diagnostic Reagents, catalog listing products for sale by Sigma Chemical Company, St. Louis, MO, 1990, p. 113.
(Sigma (II)), Biochemicals and Organic Compounds for Research and Diagnostic Clinical Reagents, catalog listing products for sale by Sigma Chemical Company, St. Louis, MO, 1990, p. 662.
M. R. Webb, "The Stereochemical Course of Nucleoside Triphosphatase Reactions," Meth. Enzymology, 87, 301–316 (1982).

Primary Examiner—John Kight
Assistant Examiner—L. Eric Crane
Attorney, Agent, or Firm—Nixon & Vanderhye

[57] ABSTRACT

Nucleoside thiotriphosphates carrying $^{32}$P in the gamma-thiophosphate group, prepared by reaction between a nucleoside diphosphate and a $^{32}$P labelled thiophosphate salt, are used as thiophosphorylating agents for antibodies that bind to tumour-associated antigens. The labelled thiotriphosphates can be used to introduce a therapeutically useful $^{32}$P atom into an antibody that has been modified by the incorporation into its structure of a peptide region capable of acting as a substrate for a phosphokinase. The resulting labelled antibody can then be used for injection in anti-tumour therapy and has clinical advantages over the corresponding phosphorylated analogue.

2 Claims, No Drawings

(GAMMA)-[$^{32}$P](GAMMA)-THIORIBONUCLEOSIDE-5$^1$-TRIPHOSPHATES

This is a Rule 60 continuation of application Ser. No. 08/077,962, filed Jun. 18, 1993, now abandoned, which is a continuation of Ser. No. 07/768,572, filed Sep. 23, 1991, now abandoned.

This invention relates to the radio-labelling of proteins and is specifically concerned with the labelling of monoclonal antibodies and other proteins with $^{32}$P. The term "protein" as used herein encompasses polypeptides.

The concept of using monoclonal antibodies, and other proteins as delivery vehicles for the targeting of drugs is already established. Practical difficulties exist however when it comes to attaching the drug to the monoclonal antibody or other delivery system since this must be done in such a way that the activity of the drug is retained and, at the same time, the specificity of the monoclonal antibody or other delivery system is maintained. At a practical level, this places considerable restriction upon those chemical and biological methods theoretically available for the linking of the drug to the delivery system as many conventional reaction conditions will destroy either or both of the drug activity and delivery system specificity.

Radiation therapy is now well-established as one possible method of treatment of certain cancer conditions and the attachment of the radio-isotopes of iodine and a variety of metals, e.g. indium and yttrium to antibodies is currently being investigated for this purpose. The radionuclide $^{32}$P is, in many ways, a particularly advantageous radionuclide for use against certain types of solid tumours with relatively poor blood supply since $^{32}$P has a reasonably short half-life of 14 days and it is a pure beta-emitter with a particle energy of 1.7 MeV. However, it has not been possible to attach $^{32}$P to antibodies by the methods that have been used previously for the attachment of other radio-isotopes.

We have now found a method by which a monoclonal antibody or similar targeting molecule can be structurally modified so that it can readily and swiftly have attached to it $^{32}$P under mild reaction conditions that maintain the specificity of the targeting molecule so as to give a $^{32}$P labelled material.

Our published UK Patent Application GB-A-2186579 describes a method for modifying a protein that will bind with a tumour-associated structure such as protein, glycolipid or carbohydrate, comprising the introduction into the binding protein of a peptide region, which is capable of acting as a substrate for a phosphokinase. We have now found that the resulting modified binding protein can then be $^{32}$P labelled by reacting it with a modified nucleoside triphosphate in which the gamma phosphate group is replaced by a thiophosphate group and in which at least the gamma thiophosphate group is $^{32}$P labelled, in the presence of a phosphokinase. This method gives rise to a binding protein (targeting molecule) carrying a $^{32}$P label.

The thiophosphorylating agent used in our invention is a nucleoside triphosphate having the gamma phosphate group replaced by a thiophosphate group and having a $^{32}$P label on the gamma thiophosphate group. Such thiophosphorylating agents are new compounds and form part of this invention. It is desirable to label as many of the gamma P atoms as possible, in practice at least 10% and preferably at least 50% of the gamma P atoms should be present as $^{32}$P.

Our earlier-mentioned UK Patent Application describes the $^{32}$P labelling of the modified binding protein by reacting it with a $^{32}$P labelled gamma nucleoside triphosphate in the presence of the phosphokinase.

A disadvantage of this procedure is that although the phosphate-serine (or threonine) bond produced during the phosphorylation of the modified protein is relatively stable in isolated plasma, toxic $^{32}$PO$_4$ is released following metabolic breakdown of the conjugate in vivo. We believe that the replacement of gamma labelled $^{32}$P nucleoside triphosphate by a corresponding reagent in which the P=O in the gamma phosphate (i.e. the terminal group that is transferred by the kinase) has been replaced by a P=S results in the formation of a thiophosphorylated serine (or threonine) which is more stable in vivo and less likely to breakdown to release toxic metabolites.

According to the present invention, we provide a compound of the general formula:

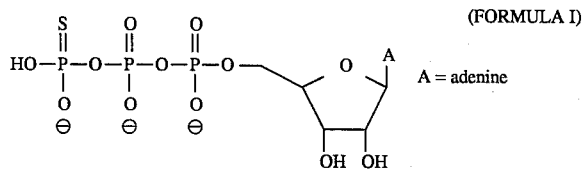

in which A represents a nucleoside residue, and the phosphorus in the gamma-thiophosphate group is $^{32}$P.

A preferred compound of the invention is [gamma-$^{32}$P]-adenosine-5'-0-(3-thiotriphosphate), hereinafter designated [gamma-$^{32}$P]ATP-gamma S and having the formula I

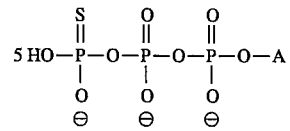

(FORMULA I)

A = adenine

The nucleoside thiotriphosphates of the invention can be prepared by enzymatic thiophosphorylation of a nucleoside diphosphate of the formula

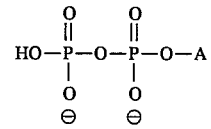

where A is defined above with a $^{32}$P thiophosphate. The thiophosphate can be a metallic thiophosphate, particularly an alkali metal or alkaline earth metal thiophosphate or an organic thiophosphate such as an amine thiophosphate where the amine is mono or disubstituted, e.g. methylamine or dimethylamine. The reaction between the nucleoside diphosphate and the $^{32}$P labelled thiophosphate may be carried out enzymatically, for example under the conditions disclosed by Cassidy and Kerrick, Biochim. et Biophys. Acta, 565 (1979), 209–213. Thus, this reaction can be carried out in the presence of a mixture of glyceraldehyde phosphate dehydrogenase, 3-phosphoglycerokinase and lactate dehydrogenase. Further guidance on the selection of appropriate enzymes for this thiophosphorylation can be found in Walseth and Johnson, Biochim. et Biophys. Acta, 562 (1979), 11–31.

The thiophosphorylation of the invention produces an aqueous solution containing the desired $^{32}$P thiotriphosphate nucleoside ester. This solution can be used without further purification to thiophosphorylate the binding protein by the procedures described below. In certain circumstances, it may be desirable to inactivate any residual enzyme from the thiophosphorylation of the diphosphate, e.g. by heat treatment at 60° C. for at least 5 minutes, prior to the final phosphorylation of the binding protein in the presence of the phosphokinase.

The binding protein will normally be a monoclonal antibody that will bind with a tumour-associated antigen, for example antigens associated with solid tumours with relatively poor blood supplies. Such solid tumours include those found in the colon, ovaries and lungs and monoclonal antibodies to such tumour-associated antigens are already known and have already been used as delivery vehicles for other anti-tumour agents. Such known antibodies can be linked to $^{32}$P by the techniques of the present invention.

More generally, the binding protein may be any protein that will bind with tumour-associated protein (or other tumour-associated structure such as a glycolipid or carbohydrate) where the tumour is one susceptible to high-energy beta particles and, in addition to monoclonal antibodies, the first protein could be, for example, an Fab fragment or a hormone or similar peptide that will bind to an appropriate receptor site identified on certain types of tumour cell e.g. melanocyte-stimulating hormone, epithelial growth factor, interferons and mitogenic peptides such as bombesin.

The structural modification of the binding protein introduces a peptide region capable of acting as a substrate for the phosphokinase so that when the structurally modified "binding protein" which can be regarded as a "protein"/substrate conjugate is brought into contact with the $^{32}$P containing thiophosphorylating agent in the presence of a phosphokinase, the enzyme can catalyse the transfer of $^{32}$P from the thiophosphorylating agent into the substrate region of the conjugate.

Present availability points to the use of serine/threonine kinases as the phosphokinase. Such materials are now commercially available from the Sigma Company e.g. bovine heart protein kinase.

A hepta peptide known as Kemptide and having the structure Leu.Arg.Arg.Ala.Ser.Leu.Gly is now commercially available and is known to be a satisfactory substrate for the bovine heart protein kinase. We have now surprisingly found that if the Kemptide structure is grafted onto a monoclonal antibody, not only is the specificity of the monoclonal antibody unaffected but also that the ability of the monoclonal antibody/Kemptide conjugate to act as a substrate for the kinase is unimpaired and that thiophosphorylation can still proceed.

One practical benefit of our new technique is that the monoclonal antibody or other protein can be partially prepared for thiophosphorylation by conjugation with the heptapeptide and the thiophosphorylation left until immediately before the radio-labelled molecule is to be administered to the patient.

The concept of the present invention does not depend upon the use of the specific heptapeptide Kemptide and indeed, any peptide can be used provided it is capable of acting as a substrate for the phosphokinase. If the phosphokinase is the serine/threonine kinase derived from bovine heart then the main structural requirement for the substrate molecule appears to be that there be an area of positive charge, e.g. arising from arginine and/or lysine residues, close to the serine and/or threonine residues in the substrate. Kemptide is one such substrate but we have worked with other similar molecules in which we have replaced the leucine residue at the N-terminus of Kemptide by a lysine-tyrosine dipeptide to give an octapeptide Lys.Tyr.Arg.Arg.Ala.Ser.Leu.Gly we have called Foxtide I. The advantages of Foxtide I over Kemptide are that conjugating the substrate molecule to the antibody molecule is facilitated by the existence of the lysine residue at the N-terminus while the presence of the tyrosine molecule gives ultra-violet "visibility" to the substrate molecule facilitating purification and identification.

We have also developed another substrate molecule meeting the general requirements set out above but which is a decapeptide of the structure: Cys.Arg.Arg.Lys.Ala.Ser.Gly.Pro.Pro.Val. We have designated this decapeptide Foxtide II. Foxtide II has advantages over Kemptide for our purposes in that the serine residue can be thiophosphorylated more quickly than can the serine residue in Kemptide under otherwise similar reaction conditions in the presence of bovine heart protein kinase. Additionally, the cysteine residue at the N-terminus facilitates conjugation with the monoclonal antibody or other first protein through the SH grouping in the terminal residue. Foxtide I and Foxtide II may be prepared by conventional solid state peptide synthesis on a Merrifield resin.

The substrate molecules discussed so far are all substrates for serine/threonine kinases but other types of phosphokinases are known and can be used with the appropriate substrate. For example, phosphokinases which are tyrosine kinases are known and substrates for such tyrosine kinases are known in which the enzyme brings about thiophosphorylation of the tyrosine residue. Examples of such tyrosine kinases include those contained in Lymphoma cell extracts as described by Casnellie et al. PNAS, 1982, 79, 282–6. An example of a substrate for the tyrosine kinases is:

Ile-Glu-Asp-Asn-Glu-Tyr-Thr-Ala-Arg-Gln-Gly.

The kinase substrates used in the present invention can be of any molecular size. The tendency is to use a substrate which is as small as possible since the only requirement is to have a thiophosphorylatable residue, e.g. serine, threonine or tyrosine which, depending upon the enzyme being used, may need to be in a close relationship to the area of positive charge. Practicalities such as the cost of synthesis and ease of purification will therefore point to the use of small peptides containing up to about 20 amino acid residues but larger substrates could be used, bearing in mind that the larger the substrate the more likely it is to interfere with the properties of the final first protein/substrate conjugate.

Chemical methods can be used for the conjugation of the substrate molecule to the monoclonal antibody or other binding protein. Essentially, it is necessary to bring about activation to an appropriate level of reactive groupings in the first protein and in the substrate molecule so that the necessary bonds can be formed so as to bring about conjugation while, at the same time, avoiding the use of reaction conditions that will cause modification of the specificity of the first protein in relation to the tumour associated protein and the capacity of the substrate molecule to act as a substrate during the subsequent phosphokinase thiophosphorylation.

We have found that satisfactory linking of the substrate molecule to the targeting molecule (the binding protein) can be achieved using appropriate hetero-bifunctional protein crosslinking agents. For example, the targeting molecule may be reacted with N-succinimidyl-3-(2-pyridyldithio)propionate (SPDP) followed by reduction with dithiothreitol. The reaction with SPDP introduces the dithiopropionyl group onto a side-chain amino group of a lysine residue in the targeting molecule while the subsequent reduction step converts the dithio grouping into a terminal thiol group. This terminal thiol group provides the reactive site for introduction of the substrate molecule.

The substrate molecule can be activated for conjugation to the targeting molecule for example by reacting the alpha-amino group of the terminal leucine residue of Xemptide with the corresponding N-hydroxysuccinimidyl esters to give for example an iodoacetamide or a phenyl maleimide which can then react with the thiol group of the thiopropionamide residue introduced on the targeting molecule so that the substrate molecule becomes attached to the targeting molecule through a short bridging group including a thio link.

For conjugation with a substrate molecule which has a reactive thiol group, such as Foxtide II, the first protein may be activated by reacting it with e.g. SMPB [succinimidyl-4-(p-maleimidophenyl)butyrate]. Other reagents that can be used for this purpose include MBS (m-maleimidobenzoyl-N-hydroxy succinimide ester), SMCC [succinimidyl]-4-(N-maleimidomethyl)-cyclohexane-1-carboxylate] and SIAB [N-succinimidyl-(4-iodoacetyl)aminobenzoate], all of which are commercially available.

In addition to the conventional synthetic methods described above for producing the protein/substrate conjugate, the appropriate substrate sequence may be integrated into an appropriate position within the primary structure of the first protein by using genetic engineering techniques.

The targeting molecule/substrate molecule conjugates are stable materials that can be stored for prolonged periods of time at room temperature or slightly below, e.g. 0° to 20° C. We have found that, after conjugation of the targeting molecule with the substrate molecule using hetero-bifunctional protein crosslinking agents, the specificity of the targeting molecule and the substrate capacity of the substrate molecule is retained both initially and after prolonged storage at 0° to 20° C.

One of the benefits of the present invention is that the targeting molecule/substrate molecule conjugate can be stored in this form for prolonged periods of time prior to use and that it can be easily thiophosphorylated to introduce the $^{32}P$ function immediately prior to use in a patient. The thiophosphorylation itself can be carried out by any conventional phosphokinase/thiophosphorylating agent system and we have found that satisfactory results can be readily achieved with bovine heart protein kinase and a thiophosphorylatable serine or threonine residue in the substrate portion of the conjugate. As an alternative to $^{32}P$-gamma-ATP-gamma S, one can also use thiophosphates based on other nucleosides such as $^{32}P$-gamma-guanidine 5'-0-(3-thiotriphosphate) as thiophosphorylating agent used in association with the appropriate phosphokinase. These thiophosphorylating agents may also be used in association with the appropriate phosphokinases to introduce $^{32}P$ onto the tyrosine residue in conjugates having a tyrosine residue in the substrate portion.

Although the present invention is primarily designed to facilitate enzymatic thiophosphorylation of the thiophosphorylatable amino acid residues in the substrate portion of the conjugate, chemical thiophosphorylation would also be possible.

Once the thiophosphorylation of the targeting molecule/substrate molecule conjugate has been completed, the $^{32}P$ labelled material can be purified by standard chromatographic techniques such as gel filtration, e.g. on a Sephadex column equilibrated with phosphate buffered saline or by affinity chromatography e.g. using a protein-A column. The $^{32}P$ conjugate solution obtained in this way may then be filtered (0.22μ) and is then in a suitable form for administration.

According to a further feature of the invention, we provide a pharmaceutical composition, particularly one for parenteral administration, comprising a pharmaceutically acceptable diluent, and a $^{32}P$-labelled thiophosphorylated protein that will bind with a tumour-associated structure.

Once a trace dose of radiolabelled binding protein is shown to target preferentially for a tumour as compared to normal tissue, then the $^{32}P$-labelled thiophosphorylated binding protein may be given to the subject intravenously or into various body regions e.g. by intraperitoneal, intrapleural or intra-arterial infusion. A suitable therapeutic dose will contain from 10–50 mCi and preferably about 30 mCi per patient in a single treatment.

The use of the $^{32}P$-labelled thiophosphorylated binding protein according to the invention has the advantage that the procedures for protection during handling and preparing the radioactive products are simplified, external radiation doses to staff are reduced and storage and disposal problems are simplified by the non-volatile nature of the material. $^{32}P$ has the advantages over other radioactive isotopes, for example $^{131}I$, in that a patient can receive a higher dose rate with $^{32}P$-labelled binding protein since the relative activity concentration required to deliver a specific dose to a target is less than that required for $^{131}I$; the unit dose delivered to a particular target tissue using phosphorus-labelled targeting molecules is, for example, approximately twice that delivered when using $^{131}I$ labelled targeting molecules. Moreover the effects of this radiation therapy on uninvolved tissues are reduced significantly by the absence of penetrating gamma radiation.

Damage to uninvolved tissues may be minimised by administration of $^{31}P$-orthophosphate salts for a period of several weeks following treatment with the $^{32}P$-labelled binding protein. The use of radioprotective agents such as Ethyol (WR2721) may also be advantageous.

The most sensitive normal tissue is the bone marrow and the application of marrow transplantation is also within the scope of this invention to allow the use of very high doses of $^{32}P$-labelled thiophosphorylated binding protein. Additionally cytokines such as granulocyte/macrophage-colony stimulating factor (GM-CSF) and the interleukins can be used for stimulating recovery of damaged bone marrow.

The $^{32}P$-labelled thiophosphorylated binding proteins are of interest in the treatment of, for example, ovarian cancer, colon metastases to the liver, malignant pleural effusions and brain tumours.

The following Examples are given to illustrate the way in which the invention can be put into practice using, as targeting molecules, monoclonal antibodies that will bind to solid tumours implanted in mice.

EXAMPLE 1

Introduction of an iodoacetyl group into the peptide receptor molecule "Kemptide" (Leu. Aru.Arg.Ala.Ser.Leu.Gly)

N-Succinimidyl-2-iodoacetate (0.75 mg, 2 eq.) in dry dimethyl formamide (DMF, 62.5 μl) was added to a solution of "Kemptide" (1.5 mg) in water (60 μl) which had first been diluted with methanol (40 μl). After incubation for one hour at room temperature, the reaction was shown to be complete by analysis of a sample with thin layer chromatography (TLC) (6065 Cellulose plates, Eastman, eluting with 1-butanol: water: acetic acid: pyridine in the proportions 50: 40: 2:32 v/v)—ninhydrin staining demonstrated the removal of the free primary amino groups. The reaction mixture was then used directly for coupling to the thiopropylated antibody as described in Example 2.

EXAMPLE 2

Introduction of a thio group into OX7 antibody and subsequentcoupling with iodoacetyl "Kemptide"

A solution of N-succinimidyl-3-(2-pyridyldithio)propionate (SPDP) (44 μl of a stock solution of 3.1 mg/ml in dry DMF) was added to a solution of OX7 monoclonal antibody (7.8 mg in borate buffer 1.0 ml, 0.05M sodium borate containing 0.1M sodium chloride and 0.5% v/v 1-butanol; pH 9.0). OX7 is a murine antibody that recognises the murine AKR lymphoma. The molar ratio of SPDP to immunoglobulin was 8:1. After incubation at room temperature for one hour, the reaction mixture was desalted on a G50 'Sephadex' column (60 ml) which had been equilibrated in acetone buffer (0.1M sodium acetate containing 0.1M sodium chloride and 1 mM ethylene diamine tetraacetic acid (EDTA); pH 4.5). Analysis of the eluted protein by the standard method of Carlsson et al., (Biochem J. 1978, 173,723) revealed that an average of 4.6 dithiopropyl groups had been introduced per IgG molecule. The protein solution (5.6 ml) was then incubated with dithiothreitol (275 μl of molar stock solution to give a final concentration of 50 mM) for one hour at room temperature and then desalted on a G50 'Sephadex' column (60 ml) equilibrated in nitrogen-flushed phosphate buffer (0.1M disodium hydrogen phosphate buffer (pH 7.5) containing 0.1M sodium chloride and 1 mM EDTA). The eluted protein was immediately concentrated again by 'Amicon' ultrafiltration to 1.0 ml, 6.3 mg/ml, diluted with DMF (200 μl) and treated with the iodacetylated Kemptide solution (30 μl, prepared as described in Example 1). This gave a final ratio of 2.5 iodoacetyl residues per thiopropyl group. The reaction mixture was incubated at room temperature for 24 hours and any remaining unreacted thiol groups were then blocked by the addition of a solution of N-ethylmaleimide (5 mg) in DMF (100 μl). After a further hour, the reaction mixture was applied to a G50 'Sephadex' column (60 ml) equilibrated in the "enzyme buffer" (50 mM potassium hydrogen phosphate (pH 7.0) containing 5 mM magnesium chloride and 0.25 mM EGTA [ethyleneglycol-bis-(beta-aminoethyl ether)-N,N,$N^1$,$N^1$-tetraacetic acid]) and the eluted protein concentrated to 1 mg/ml by 'Amicon' ultrafiltration, filtered (0.22 μ) and stored at 4° C.

EXAMPLE 3

Retention of antibody function by OX7-'Kemptide' conjugate

Solutions of OX7-Kemptide conjugate (50 μl, prepared as described in Example 2) at various concentrations were added to aliquots of AKR-A mouse lymphoma cells (1 ml at $10^6$ cells/ml) in phosphate buffered saline (PBS) containing bovine serum albumen (BSA) (2 mg/ml) and sodium azide (0.05%). After incubation at 37° C. for 30 minutes, the cells were washed twice with the PBS solution and the resultant cell pellets treated with fluorescein isothiocyanate-labelled rabbit anti-mouse antibody (Miles Labs.), diluted 1:32 from stock After incubation for 30 minutes at 37° C., the cells were washed in PBS/BSA/azide solution and finally suspended in 1 ml of the buffer solution. Flow cytometry analysis of at least $10^4$ cells at each concentration showed that conjugate and native OX7 had identical binding characteristics and there was no evidence of a decrease in affinity of the conjugated OX7. 50% saturation of the binding sites was achieved at about 60 ng/ml of OX7 or OX7-'Kemptide'.

EXAMPLE 4

Preparation of a conjugate from iodoacetyl 'Kemptide' and H17E2

H17E2 is a monoclonal antibody raised against human alphaplacental alkaline phosphatase which is normally found in placenta but is also expressed by ovarian, testicular, cervical and glioma tumour tissue. This conjugate was prepared in essentially the same way as Example 2 but using H17E2 (10 mg), SPDP (170 μg) dithiothreitol (65 μl of molar solution) and iodoacetyl-'Kemptide' (67 μl of the solution, prepared as described in Example 1). Seven thiol groups were introduced to the antibody by this procedure and a three-fold excess of iodoacetyl-Kemptide was used to maximise coupling. Any remaining unreacted thiol was then blocked with N-ethylmaleimide (6 mg) in DMF (120 μl).

EXAMPLE 5

Preparation of a conjugate from iodoacetyl 'Foxtide' and the monoclonal antibody OX7

N-Succinimidyl-2-iodoacetate (0.28 mg, 1 eq) in dry DMF (14 μl) was added to a solution of 'Foxtide I' (Lys-Tyr.Arg.Arg.Ala.Ser.Leu.Gly) (1 mg) in water (40 μl) diluted with methanol (60 μl) which was then treated with 100 μM sodium hydroxide (14 μl) giving a pH of 6.4. After incubation for one hour at room temperature, TLC followed by ninhydrin staining indicated that the reaction was complete. A sample of this reaction mixture (60 μl) was added to a solution of thiolated OX7 monoclonal antibody (650 μl, prepared as described in Example 2) and incubated at 4° C. for 72 hours. Unreacted thiol groups (if any) were then blocked by the addition of N-ethylmaleimide (5 mg) in DMF (50 μl) and after incubation for one hour, the conjugate was isolated and stored in the enzyme buffer as described in Example 2.

EXAMPLE 6

Synthesis of [gamma-$^{32}$P]-adenosine-5'-0-(3-thiotriphosphate)

The following reagents were introduced into a 150 ml flask:

Tris buffer, pH 8.0, 50 mmol
$MgCl_2$, 12 mmol
Dithiothreitol, 6 mmol
DL-glyceraldehyde 3-phosphate, 8 mmol
β-AND, 0.5 mmol
Adenosine diphosphate, 8.6 mmol
Sodium pyruvate, 20 mmol
$^{32}$P-sodium thiophosphate, 1.7 mmol–1 mCi activity
Ethylenediamine tetraacetic acid disodium salt, 0.1 mmol
Glyceraldehyde phosphate dehydrogenase, 1.6 units/ml
3-phosphoglycerokinase, 1 unit/ml
Lactate dehydrogenase, 2.75 units/ml The total volume of this mixture was 50 ml and its pH was adjusted to 7.5 with sodium hydroxide after the addition of the pyruvate. The reaction was allowed to proceed overnight at room temperature to give an aqueous solution containing the required [gamma-$^{32}$P]-adenosine 5'-0-(3-thiotriphosphate).

EXAMPLE 7

Thiophosphorylation of OX7-Kemptide

OX7-Kemptide stock solution (70 μl at 1 mg/ml prepared as described in Example 2), +5 "enzyme buffer" (30μl), 250 mM dipotassiumhydrogen phosphate (pH 7.0) containing 25 mM magnesium choride and 1.25 mM EGTA was added to 1 mCi of the labelled thiotriphosphate described in Example 6 followed by bovine heart protein kinase (5μl, 50 units, sigma). The reaction was incubated for 30 minutes at 37° C. and the protein was then desalted using $G_{50}$ Sephadex column (10 ml) equilibrated in phosphate buffered saline which had been prewashed in buffered saline containing bovine serum albumin (2 mg/ml). The material eluted from the column was $^{32}$P labelled OX7-Kemptide.

What is claimed is:

1. A compound of the formula:

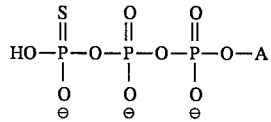

in which A represents a nucleoside residue, and the phosphorus in the gamma-thiophosphate group is $^{32}$P.

2. A compound according to claim 1, wherein A is an adenosine residue.

* * * * *